US008257755B2

(12) United States Patent
Sasaki et al.

(10) Patent No.: US 8,257,755 B2
(45) Date of Patent: Sep. 4, 2012

(54) METABOLIC SYNDROME-IMPROVING AGENT AND MEDICINE, SUPPLEMENT, FUNCTIONAL FOOD AND FOOD ADDITIVE CONTAINING THE SAME

(75) Inventors: Takao Sasaki, Kyoto (JP); Masamichi Yano, Shizuoka (JP)

(73) Assignee: ARKRAY, Inc., Kyoto (JP)

( * ) Notice: Subject to any disclaimer, the term of this patent is extended or adjusted under 35 U.S.C. 154(b) by 271 days.

(21) Appl. No.: 11/795,638

(22) PCT Filed: Jan. 20, 2006

(86) PCT No.: PCT/JP2006/300865
§ 371 (c)(1),
(2), (4) Date: Jul. 19, 2007

(87) PCT Pub. No.: WO2006/077975
PCT Pub. Date: Jul. 27, 2006

(65) Prior Publication Data
US 2008/0132566 A1 Jun. 5, 2008

(30) Foreign Application Priority Data
Jan. 21, 2005 (JP) ................................. 2005-014385

(51) Int. Cl.
*A61K 36/752* (2006.01)
*A61K 31/235* (2006.01)
(52) U.S. Cl. ....................................... 424/736; 514/454
(58) Field of Classification Search .................. 424/736; 514/454
See application file for complete search history.

(56) References Cited

U.S. PATENT DOCUMENTS

| 6,509,371 | B1 | 1/2003 | He et al. | |
|---|---|---|---|---|
| 6,652,892 | B2 * | 11/2003 | McGenity et al. | ................. 426/2 |
| 2003/0054015 | A1 | 3/2003 | Haze et al. | |
| 2006/0127412 | A1 | 6/2006 | Kakuo et al. | |

FOREIGN PATENT DOCUMENTS

| JP | 2002-193824 | 7/2002 |
|---|---|---|
| JP | 2004-154122 | 6/2004 |
| JP | 2005-194252 | 7/2004 |
| JP | 2004-217532 | 8/2004 |
| JP | 2005-272456 | 10/2005 |
| WO | 99/21570 | 5/1999 |
| WO | 01/80870 | 11/2001 |
| WO | 03/059309 | 7/2003 |
| WO | WO 03086423 A1 * | 10/2003 |

OTHER PUBLICATIONS

McHale et al., "The oxygen heterocyclic compounds of citrus peel oils", Journal of Essential Oil Research, vol. 1, No. 4, pp. 139-149 (1989).*
Pisarik, "Blood Pressure-Lowering Effect of Adding Grapefruit Juice to Nifedipine and Terzosin in a Patient with Severe Renovascular Hypertension", Archives of Family Medicine, vol. 5, No. 7, pp. 413-416 (Jul./Aug. 1996).*
Buiarelli, et al., "Analysis of Bitter essential oils from orange and grapefruit by high-performance liquid chromatography with microbore columns", Journal of Chromatography A. 730 (1996) 9-16.
Morlière, et al., "Photoreactivity of 5-Geranoxypsoralen and Lack of Photoreaction with DNA", Photochemistry and Photobiology, vol. 53, No. 1, pp. 13-19, 1991.
Kawaii, et al., "Isolation of Furocoumarins from Bergamot Fruits as HL-60 Differentiation-Inducing Compounds", J. Agic. Food Chem. 1999, 47, 4073-4078.
Matsuzawa, "Concept of Metabolic Syndrome and Molecular Mechanism", The Journal of Therapy, Nov. 2004, vol. 86, No. 11, pp. 011-016 with a partial English translation.
Fujioka, et al., "The Effects of Grapefruit on Weight and Insulin Resistance: Relationship to the metabolic syndrome", Diabetes, American Diabetes Association, US, vol. 53, No. Suppl. 2, Jun. 1, 2004, p. A594, XP008115930, ISSN: 0012-1797.
Kurowska, et al., "Hypocholesterolemic Effects of Dietary Citrus Juices in Rabbits", Nutrition Research, vol. 20, No. 1, Jan. 1, 2000, pp. 121-129, XP000999077, ISSN: 0271-5317.
Luquet, et al., "Roles of peroxisome proliferators-activated receptor delta (PPARδ) in control of fatty acid catabolism. A new target for the treatment of metabolic syndrome", Biochimie, vol. 86, No. 11, Nov. 1, 2004, pp. 833-837, XP 004689093, ISSN: 0300-9084.
Office Action in corresponding European Patent Application No. 06712090.7 (mailed Jul. 15, 2011).
Goosen et al., "Bergamottin contribution to the grapefruit juice-felodipine interaction and disposition in humans", Clinical Pharmacology & Therapeutics, 76(6):607-617 (2004).

* cited by examiner

*Primary Examiner* — Kevin E Weddington (74) *Attorney, Agent, or Firm* — Morgan, Lewis & Bockius LLP (57) ABSTRACT

A metabolic syndrome relieving agent that is free from a problem of side effects and can be taken for a long term is provided. Bergamottin is used as an agent for relieving a metabolic syndrome. Since bergamottin has functions of activating PPARα and PPARγ, promoting the secretion of adiponectin in adipocytes and inhibiting the generation of VLDLs in hepatic cells, it is possible to prevent or treat diseases such as insulin resistance, hyperinsulinism, type 2 diabetes, obesity, visceral fat obesity, hypertension, hyperlipemia, arteriosclerosis and the like and thus prevent or treat the metabolic syndrome. Also, as understood from the fact that citrus fruits such as a grapefruit or the like containing bergamottin have been eaten for many years, they have no problems in terms of safety and have a low calorie content, and therefore, they can be taken for a long term. Further, since bergamottin is tasteless and odorless, it does not impair the unique taste of a food when added to this food, so that it can be added to foods and taken.

12 Claims, 2 Drawing Sheets

METABOLIC SYNDROME-IMPROVING AGENT AND MEDICINE, SUPPLEMENT, FUNCTIONAL FOOD AND FOOD ADDITIVE CONTAINING THE SAME

TECHNICAL FIELD

The present invention relates to a metabolic syndrome relieving agent, and drugs, supplements, functional foods and food additives containing the same.

BACKGROUND ART

For the past several years, the concept of metabolic syndrome has been expounded by WHO (the World Health Organization) as well as the National Cholesterol Education Program (NCEP) in the United States. The metabolic syndrome is the state in which various diseases causing arteriosclerosis, for example, visceral fat obesity, insulin resistance, diabetes, hyperlipemia, hypertension, etc. cluster together, so that angina pectoris, myocardial infarction or the like occurs easily. It is considered that the metabolic syndrome is ascribable to visceral adiposity and hypertrophic adipocytes.

The following two mechanisms have been revealed as how the visceral adiposity is associated with the development of diabetes, hyperlipemia, hypertension or the like. One is the mechanism in which a large amount of glyceride accumulated in visceral fat is decomposed in the fasting state, and a large amount of free fatty acid and glycerol, which are products of the decomposition, are released and flow excessively into the liver, leading to hyperlipemia, hyperglycemia and hyperinsulinism. The other is the mechanism in which the visceral adiposity causes abnormal adipocytokine secretion, which inhibits the secretion of adiponectin, for example, so that diabetes, arteriosclerosis or the like occurs (for example, see Non patent document 1). It has been revealed that the adiponectin activates a peroxisome proliferator-activated receptor (PPAR)α and AMP kinase so as to promote fatty acid burning or the like, thus decreasing the content of neutral fats in tissue and thereby, for example, relieving the insulin resistance or the like. Further, there has been a report that, besides the above, the adiponectin has antidiabetic, anti-arteriosclerotic, antihypertensive and anti-inflammatory effects.

On the other hand, PPARs, which are intranuclear receptors, are said to be associated with the relief of insulin resistance, hyperinsulinism, type 2 diabetes as well as obesity, hypertension, hyperlipemia and arteriosclerosis. PPARs are known to have three types, i.e., α, δ and γ, and several subtypes. PPARα is expressed mainly in the hepatic cells and also in other cells such as myocardial cells and gastrointestinal cells, and concerned with fatty acid oxidation, ketogenesis and apolipoprotein generation. Although PPARγ is not considered to have tissue specificity and is expressed throughout the body, it is expressed notably in large intestinal cancer cells. PPARγ can be classified into two subtypes, i.e., type γ1 and type γ2. The type γ1 is expressed in adipose tissues, immune system tissues, the adrenal gland and the small intestine, whereas the type γ2 is expressed specifically in adipocytes and plays an important role in differentiation induction of the adipocytes and fat synthesis.

The number of patients afflicted with the metabolic syndrome tends to increase mainly in developed countries. Accordingly, there is an urgent need for a metabolic syndrome relieving agent that has excellent safety and can be taken over a long term.

Non patent document 1: Yuji MATSUZAWA, "Concept of Metabolic Syndrome and Molecular Mechanism," The Journal of Therapy, November 2004, Vol. 86, No. 11, pages 011-016.

DISCLOSURE OF INVENTION

Problem to be Solved by the Invention

It is an object of the present invention to provide a metabolic syndrome relieving agent that is free from a problem of side effects and can be taken for a long term.

Means for Solving Problem

In order to achieve the above-mentioned object, an agent for relieving a metabolic syndrome according to the present invention contains bergamottin. The metabolic syndrome includes diseases, for example, insulin resistance, hyperinsulinism, type 2 diabetes, hyperlipemia, arteriosclerosis, hypertension, obesity, visceral fat obesity and the like.

Effects of the Invention

From the viewpoints of side effects and long-term intake, the inventor of the present invention conducted a series of studies mainly on substances contained in food. In the course of the studies, the inventor found that bergamottin contained in citrus fruits had functions of activating PPARα and PPARγ, promoting the secretion of adiponectin in adipocytes and inhibiting the generation of very low-density lipoproteins (VLDLs) in hepatic cells, thus arriving at the present invention. In other words, according to the metabolic syndrome relieving agent of the present invention, since the PPAR activation promotes fat burning so as to inhibit the secretion of TNFα and free fatty acid, the state of adipocytes can be normalized, thus making it possible to prevent or treat diseases, for example, insulin resistance, hyperinsulinism, type 2 diabetes, obesity, visceral fat obesity, hypertension, hyperlipemia, arteriosclerosis and the like. Also, the metabolic syndrome relieving agent according to the present invention promotes the secretion of adiponectin in adipocytes so as to promote fatty acid burning and PPARα activation, thereby normalizing the state of adipocytes, and suppresses endangiitis or the like, thereby preventing LDLs from being taken into blood vessels, for example. Consequently, this also makes it possible to prevent or treat diseases, for example, insulin resistance, hyperinsulinism, type 2 diabetes, obesity, visceral fat obesity, hypertension, hyperlipemia, arteriosclerosis and the like. Further, since the metabolic syndrome relieving agent according to the present invention inhibits the generation of VLDLs in hepatic cells so as to suppress an increase in neutral fats, it is possible to prevent or treat diseases, for example, hyperlipemia and the like. In this way, since the metabolic syndrome relieving agent according to the present invention can prevent or treat the above-described diseases, for example, by being administered to a human and mammals other than the human, it is considered to have an excellent effect of relieving a metabolic syndrome.

Moreover, citrus fruits, for example, a grapefruit and a bergamot, containing a large amount of bergamottin have been eaten for many years and confirmed in terms of safety. Also, bergamottin has a low calorie content and, in this regard, does not cause any problem even if it is taken by a diabetic patient, an obese patient or the like for a long term.

Further, since bergamottin is tasteless and odorless, it does not impair the unique taste of a food or the like when added to this food, so that it can be added to foods and taken daily over a long term, for example.

DESCRIPTION OF THE INVENTION

The metabolic syndrome relieving agent according to the present invention has the functions of activating a PPAR, promoting the secretion of adiponectin in adipocytes, inhibiting the generation of VLDLs in hepatic cells, inhibiting the secretion of TNFα and free fatty acid in adipocytes and promoting p oxidation of fat in hepatic cells, for example. The PPAR to be activated is at least one of PPARα and PPARγ, for example, and preferably is both of them. Further, the metabolic syndrome relieving agent according to the present invention induces at least one of apoptosis, differentiation and shrinkage of an adipocyte, for example. It should be noted that the metabolic syndrome relieving agent according to the present invention may contain various additives other than bergamottin, and further may contain other components having a PPAR activating function, for example.

In the metabolic syndrome relieving agent according to the present invention, the bergamottin to be used is not particularly limited, and examples thereof include those derived from citrus fruits. In particular, bergamottin derived from a fruit juice, that derived from a fruit and that derived from a peel are preferable, and only one of or a combination of two or more of them may be used. Examples of the citrus fruits can include a grapefruit, a bergamot and the like. The bergamottin may be a product obtained by isolation and purification from the above-noted citrus fruits or may be a commercially available product, for example.

Next, a drug according to the present invention is a drug for preventing or treating a metabolic syndrome, and the drug contains the metabolic syndrome relieving agent according to the present invention. The drug according to the present invention is administered to a human and mammals other than the human, thereby making it possible to prevent or treat diseases, for example, insulin resistance, hyperinsulinism, type 2 diabetes, hyperlipemia, arteriosclerosis, hypertension, obesity and visceral fat obesity. The drug of the present invention may contain not only the metabolic syndrome relieving agent according to the present invention but also other components having a PPAR activating function and pharmaceutically acceptable additives, for example. In the drug according to the present invention, examples of its specific dosage form can include tablets, fine grains (including pulvis), capsules, solution (including syrup) and the like. The drug according to the present invention can be manufactured by using an additive or a base, etc. that is suitable for the respective dosage form as necessary according to a regular method described in the Pharmacopoeia of Japan or the like. Also, a route of administration is not particularly limited but can be, for example, an oral administration or a parenteral administration. Examples of the parenteral administration can include intraoral administration, tracheobronchial administration, intrarectal administration, subcutaneous administration, intramuscular administration, intravenous administration and the like.

Now, a supplement according to the present invention is a supplement for preventing or relieving a metabolic syndrome, and the supplement contains the metabolic syndrome relieving agent according to the present invention. The supplement according to the present invention is taken by a human and mammals other than the human, thereby making it possible to prevent or relieve diseases, for example, insulin resistance, hyperinsulinism, type 2 diabetes, hyperlipemia, arteriosclerosis, hypertension, obesity and visceral fat obesity. The supplement of the present invention may contain not only the above-mentioned metabolic syndrome relieving agent according to the present invention but also various additives, other supplements and the like, for example, other components having a PPAR activating function, various vitamins such as, vitamin C, amino acids and oligosaccharides. The supplement according to the present invention may be in any form without particular limitation, which can be, for example, tablets, fine grains (including pulvis), capsules, solution (including syrup) or the like.

Next, a functional food according to the present invention is a functional food for preventing or relieving a metabolic syndrome, and the functional food contains the metabolic syndrome relieving agent according to the present invention. The functional food according to the present invention is taken by a human and mammals other than the human, thereby making it possible to prevent or relieve diseases, for example, insulin resistance, hyperinsulinism, type 2 diabetes, hyperlipemia, arteriosclerosis, hypertension, obesity and visceral fat obesity. The functional food of the present invention may contain not only the above-mentioned metabolic syndrome relieving agent according to the present invention but also various additives and the like and may contain, for example, other components having a PPAR activating function. Incidentally, the functional food according to the present invention may be in any form without particular limitation, which can be, for example, noodles, confectionery, functional drinks or the like.

Now, a food additive according to the present invention is a food additive for preventing or relieving a metabolic syndrome, and the food additive contains the metabolic syndrome relieving agent according to the present invention. The food additive according to the present invention is taken by a human and mammals other than the human, thereby making it possible to prevent or relieve diseases, for example, insulin resistance, hyperinsulinism, type 2 diabetes, hyperlipemia, arteriosclerosis, hypertension, obesity and visceral fat obesity. The food additive of the present invention may contain not only the above-mentioned metabolic syndrome relieving agent according to the present invention but also various additives and the like and may contain, for example, other components having a PPAR activating function. The food additive according to the present invention may be in any form without particular limitation, which can be, for example, liquid, paste, powder, flakes, granule or the like. Moreover, the food additive according to the present invention includes, for example, food additives for drinks.

Next, a PPAR activator according to the present invention contains bergamottin. The PPAR activator according to the present invention also may contain components other than bergamottin. Examples of the above-noted other components include various additives, other PPAR activators and the like. The bergamottin that can be used in the PPAR activator according to the present invention is similar to that in the above-described metabolic syndrome relieving agent of the present invention.

The PPAR activator according to the present invention can be used for relieving the metabolic syndrome and treating a dermatosis or the like, for example. Examples of the dermatosis include the skin of premature infants of gestational age less than 33 weeks; atopic and seborrheic dermatitis; inflammation to mucous membranes, such as cheilitis, chapped lips, nasal irritation and vulvovaginitis; eczematous dermatitis resulting from allergic and irritant contact, eczema craquelee, radiation and stasis dermatitis; ulcers and erosions due to chemical or thermal burns, bullous disorders or vascular compromise or ischemia including venous, arterial, embolic or diabetic ulcers; ichthyoses, with or without an associated barrier abnormality; epidermolysis bullosa; psoriasis; hypertrophic scars and keloids; intrinsic aging and dermatoheliosus; mechanical friction blistering; corticosteroid atrophy; and melanoma and non-melanoma skin cancer, including lignin melanoma, basal cell carcinoma, squamous cell carcinoma, actinic keratoses, and virally induced neoplasia (warts and condylomata accuminata). When the PPAR activator according to the present invention is used for treating a dermatosis, it may be in any form without particular limitation, which can be, for example, a lotion, a solution, a gel, a cream, an emollient cream, an ointment, a spray or other forms that can be applied locally.

Next, an adiponectin secretagogue according to the present invention contains bergamottin. The adiponectin secretagogue according to the present invention may contain components other than bergamottin. The bergamottin that can be used in the adiponectin secretagogue according to the present invention is similar to that in the above-described metabolic syndrome relieving agent of the present invention.

The adiponectin secretagogue according to the present invention can be utilized for relieving the metabolic syndrome, treating a chronic liver disease such as chronic hepatitis, or the like, for example. The adiponectin secretagogue according to the present invention can inhibit liver fibrosis in a chronic liver disease such as chronic hepatitis, for example. The adiponectin secretagogue according to the present invention can be in any form without particular limitation, which can be, for example, drugs, supplements, functional foods or food additives.

Now, a use according to the present invention is a use of bergamottin for manufacturing a metabolic syndrome relieving agent. Another use according to the present invention is a use including administering bergamottin to a human and mammals other than the human for relieving a metabolic syndrome. Yet another use according to the present invention is a use of bergamottin for manufacturing a PPAR activator. The bergamottin can be similar to that in the above-described metabolic syndrome relieving agent of the present invention. Examples of the above-noted mammals include a mouse, a rat, a rabbit, a dog, a cat, a cow, a horse, a swine, a monkey and the like.

Now, a method for relieving a metabolic syndrome according to the present invention is a method including administering bergamottin to a human and mammals other than the human. The bergamottin that can be used in the relieving method according to the present invention is similar to that in the above-described metabolic syndrome relieving agent of the present invention. In the relieving method according to the present invention, the bergamottin to be administered can be in any form without particular limitation, which can be, for example, tablets, fine grains (including pulvis), capsules, solution (including syrup) and the like. Also, a method of administration is not particularly limited but can be, for example, an oral administration or a parenteral administration. Examples of the parenteral administration can include intraoral administration, tracheobronchial administration, intrarectal administration, subcutaneous administration, intramuscular administration, intravenous administration and the like.

Next, a PPAR activating method according to the present invention is a method including activating a PPAR with bergamottin. In the PPAR activating method according to the present invention, it is preferable that the PPAR is activated by bringing the bergamottin into contact with an adipocyte or the like, for example. The bergamottin that can be used in the activating method according to the present invention is similar to that in the above-described metabolic syndrome relieving agent of the present invention.

Now, it is preferable that the bergamottin in the present invention is manufactured from a material such as citrus fruits as described earlier. The following is a description of an example of this manufacturing method (J. Agric Food Chem. 1000. 47. 4073-4078).

An edible portion of a bergamot juice or the like is dispersed homogeneously in ethanol. A supernatant of the above-noted homogenate is concentrated under a reduced pressure and adsorbed by a 250 g polystyrene resin. The above-noted resin is eluted with 750 ml ethanol and then eluted with 750 ml acetone. The resultant eluate is concentrated under a reduced pressure, and an aqueous solution thereof is separated between diethyl ether and n-butanol, thus obtaining a diethyl ether eluted fraction and an n-butanol eluted fraction. The ether eluted fraction is subjected to silica gel column chromatography so as to be eluted with 20% ethyl acetone in hexane, chloroform, 20% chloroform in methanol and methanol. The fraction eluted with ethyl acetone further is purified by HPLC, thus obtaining bergamottin.

Now, examples of the present invention will be described. It should be noted that the present invention is not limited to these examples.

EXAMPLE 1

As described in the following, the present example confirmed that bergamottin was able to activate PPARγ.

CV-1 cells (cultured cells derived from kidneys of male African green monkeys) were implanted on 24-well culture plates so as to be 0.2 μg/well and cultured at 37° C. in 5% $CO_2$ for 24 hours. As a medium, DMEM (Dulbecco's Modified Eagle Medium; manufactured by GIBCO) containing 10% FBS (fetal bovine serum) and a 10 mg/mL penicillin streptomycin solution was used. Using the Lipofectamine system (trade name; manufactured by Invitrogen Corporation), pM-hPPARγ and p4×UASg-tk-luc were transfected. The above-noted pM-hPPARγ was a chimeric protein-expression plasmid binding GAL4 gene (amino acid sequence 1-147) and human PPARγ ligand-binding site gene (amino acid sequence 204-505), whereas the above-noted p4×UASg-tk-luc was a reporter plasmid containing four copies of a responsive element (UAS) of GAL 4 upstream of a luciferase gene. About 24 hours after the transfection, samples of bergamottin at respective concentrations (0.1, 1.0, 10, 50 and 100 μM) were added to the above-described media, followed by 24 hour incubation. The above-noted samples were prepared by dissolving bergamottin in dimethyl sulfoxide (DMSO). Instead of the above-noted sample, DMSO was used for non-treated control media. After the incubation, measurement was made using a Dual-Luciferase Reporter Gene Assay system (trade name; manufactured by Promega Corporation).

Similarly to the measurement group, as a control group, pM (a plasmid from which PPARγ ligand-binding site gene was removed) was used for measurement instead of pM-hPPARγ. For each sample, the ratio between average luminescence intensities of the measurement group and the control group (n=4) (measurement group/control group) was calculated, and an activity relative to the non-treatment control was determined as the PPARγ ligand activity of the sample. Table 1 below and the graph of FIG. 1 show the results.

TABLE 1

|  | Addition concentration | PPARγ ligand activity |
| --- | --- | --- |
| Non-treatment control (DMSO) | (0.1%) | 100 |
| Bergamottin | 0.1 μM | 90 ± 5.7 |
|  | 1.0 μM | 132 ± 12.0 |
|  | 10 μM | 388 ± 41.4 |
|  | 50 μM | 961 ± 72.1 |
|  | 100 μM | 1032 ± 248.3 |
|  |  | (average ± standard error) |

Figure 1:
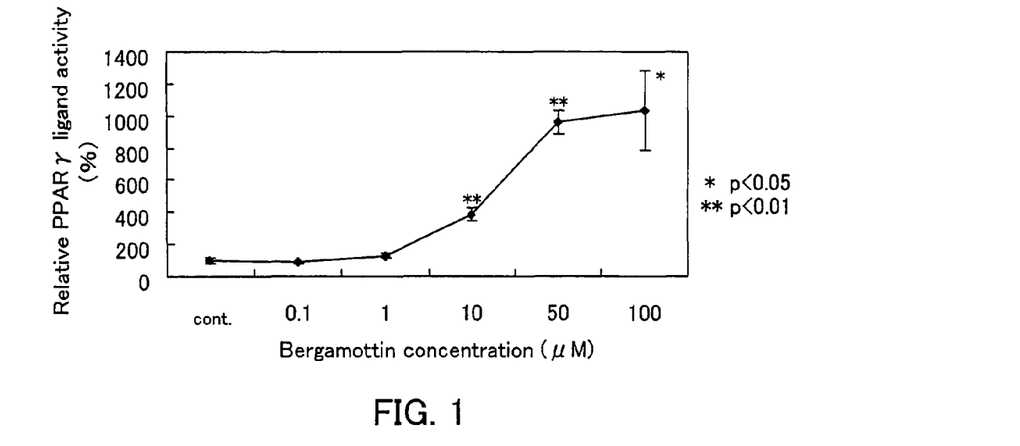
FIG. 1 is a graph showing a PPARγ ligand activity of bergamottin in an example of the present invention.

As becomes clear from Table 1 and FIG. 1 mentioned above, the bergamottin improved the activity of PPARγ such that the PPARγ activity increased along with the concentration of bergamottin. Also, this activity level was higher than that of catechin.

EXAMPLE 2

As described in the following, the present example confirmed that bergamottin was able to activate PPARα.

The PPARα ligand activity of bergamottin was measured similarly to Example 1 except that pM-hPPARα was used instead of pM-hPPARγ and the bergamottin concentrations were set to 0.1, 1.0, 5.0, 10, 20, 50 and 80 μM. Table 2 below and the graph of FIG. 2 show the results.

TABLE 2

|  | Addition concentration | PPARα ligand activity |
| --- | --- | --- |
| Non-treatment control (DMSO) | (0.01%) | 100 |
| Bergamottin | 0.1 μM | 95 ± 12.9 |
|  | 1.0 μM | 92 ± 8.0 |
|  | 5.0 μM | 118 ± 6.1 |
|  | 10 μM | 194 ± 15.0 |
|  | 20 μM | 350 ± 25.5 |
|  | 50 μM | 622 ± 79.6 |
|  | 80 μM | 558 ± 39.4 |
|  |  | (average ± standard error) |

Figure 2:
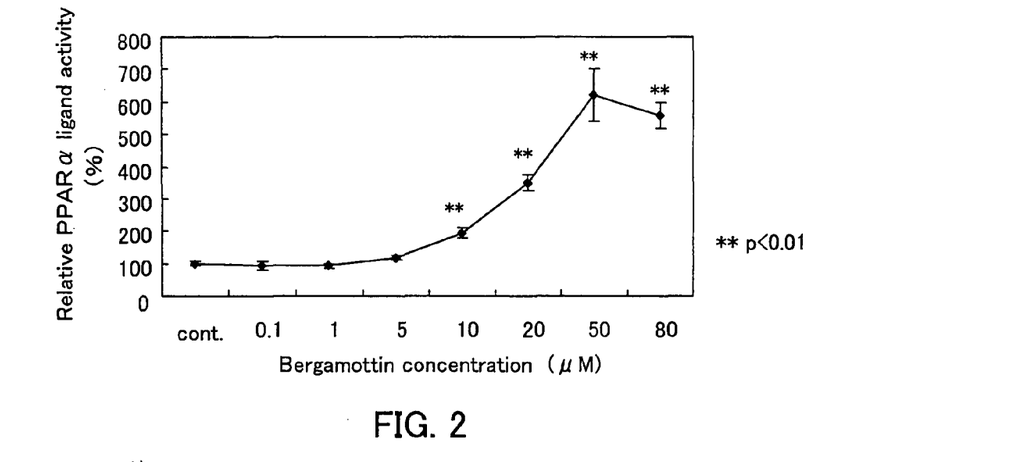
FIG. 2 is a graph showing a PPARα ligand activity of bergamottin in another example of the present invention.

As becomes clear from Table 2 and FIG. 2 mentioned above, the bergamottin improved the activity of PPARα such that the PPARα activity increased in keeping with the concentration of bergamottin.

EXAMPLE 3

As described in the following, the present example confirmed the promotion of adiponectin secretion by bergamottin.

(Differentiation Induction of Preadipocyte)

First, the following two kinds of media were prepared. Differentiation Induction Medium (0.25 μM DEX, 0.5 mM MIX, 10 μg/mL Insulin/10% FBS/DMEM)

55 mL of FBS (fetal bovine serum (manufactured by GIBCO)) was added to 500 mL of DMEM (manufactured by SIGMA) so as to prepare 10% FBS/DMEM. To this 10% FBS/DMEM, 138.75 μL of 1 mM DEX (dexamethasone)/DMSO (manufactured by Nacalai Tesque, Inc.) and 555 μL of 10 mg/mL insulin/PBS (manufactured by SIGMA) were added. Incidentally, the insulin/PBS was obtained by adding 1 N HCl to PBS in advance so as to make the solution acidic enough to allow insulin dissolution and then dissolving insulin. MIX (3-isobutyl-1-methylxanthine) (manufactured by Nacalai Tesque, Inc.) was added to a necessary amount of the above-described medium immediately before use in such a manner as to achieve 0.5 mM, thereby preparing a differentiation induction medium. Since MIX was very difficult to dissolve, it first was dissolved in a small amount of 99.5% ethanol and then added to 10% FBS/DMEM. At this time, an adjustment was made so that the final concentration of 99.5% ethanol did not exceed 1%.

Differentiation Promotion Medium (5 μg/mL Insulin/10% FBS/DMEM)

A differentiation promotion medium was prepared by adding 277.5 μL of 10 mg/mL insulin/PBS to 555 mL of 10% FBS/DMEM.

Next, culture preadipocytes 3T3-L1 were thawed, inoculated in a 100 mm dish and cultured until 3T3-L1 cells reached about 80% confluence. A single dish of 3T3-L1 that had reached about 80% confluence was subcultured to a single 6-well plate and further cultured until the 3T3-L1 cells reached confluence in the 6- well plate, and then the medium was replaced with the differentiation induction medium, followed by differentiation induction. 48 hours later, the medium was replaced with the differentiation promotion medium, and thereafter, the medium was replaced with the differentiation promotion medium every two days. 7 days after the initiation of the differentiation induction, mRNA was extracted using Sepasol-RNA I Super (trade name; manufactured by Nacalai Tesque, Inc.), and the mRNA expression amounts of 36B4, aP2 and adiponectin, which were indicators of an early period of adipocyte differentiation, were measured using Light Cycler (TM). Also, the medium 7 days after the differentiation induction was taken in an amount of 1 mL from each well, and the amount of adiponectin in the medium supernatant was measured using a mouse/rat adiponectin ELISA kit (manufactured by Otsuka Pharmaceutical Co., Ltd.).

(Quantitative Determination of mRNA Using Light Cycler™)

Extraction and Quantitative Determination of Total RNA

The medium was removed from the above-described 6-well plate, 1 mL of Sepasol(R)-RNA I Super (manufactured by Nacalai Tesque, Inc.) was added to each well, and pipetting was repeated several times so as to disperse the cells. This solution was transferred to a 1.5 mL tube and allowed to stand for 5 minutes at room temperature, and then 200 μL of chloroform was added, stirred well with a vortex stirrer and allowed to stand for 3 minutes at room temperature. The solution was cooled to 4° C. and centrifuged at 12000×g for 15 minutes. While taking great care not to disturb an interface between a phenol layer (a lower layer, yellow) and a water layer (an upper layer, colorless), the water layer alone was transferred to another tube (with a capacity of 1.5 mL). At this time, care was taken not to take proteins floating between these layers. 500 μL of isopropanol was added to the tube and mixed and allowed to stand for 10 minutes at room temperature. The solution was cooled to 4° C. and centrifuged at 12000×g for 10 minutes, followed by removing about 1 mL of the supernatant. To this precipitate, 1 mL of 75% ethanol was added and stirred to suspend the precipitate sufficiently, and then cooled to 4° C. and centrifuged at 12000×g for 10 minutes, followed by removing the supernatant. The resultant precipitate (total RNA) was dried and then dissolved in 20 μL of nuclease free water, thus measuring the concentration of mRNA using NanoDrop (manufactured by SCRUM Inc.).

Reverse Transcription

The extracted and measured mRNA solution was adjusted to have an mRNA concentration of 1 μg/μL. 1 μL of Oligo dT primer and 10 μL of the above-described RNA solution were added to 8-tube strips (with a capacity of 0.2 mL). The mixture solution was incubated in a Thermal cycler at 70° C. for 10 minutes so as to destroy higher-order structures of RNA, and transferred onto the ice and allowed to stand for at least 1 minute. Then, 11 μL of RNA sample/primer mixture solution, 5 μL of 5×reverse transcription buffer, 1 μL of RNase inhibiter, 5 μL of 2.5 mM dNTP Mix and 2 μL of Nuclease Free water were added in this order (24 μL in total).

After pre-incubation at 42° C. for 5 minutes in the Thermal cycler, 1 μL of reverse transcriptase was added, and the content of the tube was mixed well by pipetting. After incubation at 42° C. for 50 minutes and further incubation at 70° C. for 15 minutes in the Thermal cycler, the content was cooled on the ice and centrifuged mildly so as to collect the reaction solution to the tube bottom, and then frozen and stored at −20° C. Every time it was used for the Light Cycler™ measurement, it was diluted by 10 times.

Measurement using Light Cycler (TM)

All the operations described below were carried out in a clean bench. 5 μl of a plasmid solution containing fragments of the gene whose expression amount was to be measured was poured in a 0.65 mL tube and diluted by 10 times with 45 μl of water attached to Light Cycler (TM) DNA Master SYBR Green (trade name). By repeating these operations, $10^2$-time, $10^3$-time, $10^4$-time, $10^5$-time, $10^6$-time, $10^7$-time and $10^8$-time diluted solutions were produced, respectively. A dedicated capillary was set into a Light Cycler (TM) Centrifuge Adapter (trade name) using tweezers, and 18 μL each of the above-noted reagent was dispensed thereto. Further, 2 μL of water (negative control) or the 7- step diluted solution (standard) and 2 μL of 10-time diluent of cDNA serving as a measurement sample were added, and a lid was placed using tweezers. After centrifugation at 5000 rpm at 4° C. for 10 seconds, the capillary was mounted on a carousel, which then was set in a chamber and measured.

(Measurement of Adiponectin Secretion Amount Using ELISA)

The above-mentioned mouse/rat adiponectin ELISA kit had the following configuration.
Stock solution for washing
Stock solution for diluting analyte
Antibody plate (anti mouse adiponectin polyclonal antibody (rabbit) solid phase plate)
8.0 ng/mL standard product (recombinant mouse adiponectin)
Biotin labeled antibody solution (biotin labeled anti mouse adiponectin polyclonal antibody (rabbit))
Enzyme-labeled streptavidin stock solution (HRP-labeled streptavidin)
Enzyme-labeled streptavidin diluent
Substrate solution A (3,3',5,5'-tetramethylbenzidine)
Substrate solution B (hydrogen peroxide)
Reaction stop solution First, the following reagents and analyte solution were prepared.
Washing Solution The above-noted stock solution for washing and purified water were mixed in a ratio of 40 mL to 960 mL and stored at 2.8° C.
Analyte Diluent The above-noted stock solution for diluting analyte and purified water were mixed in a ratio of 50 mL to 200 mL and stored at 2.8° C.
Standard Solution The above-noted 8.0 ng/mL standard product was diluted in two steps with the above-described analyte diluent, thus preparing standard solutions having a concentration of 4.0 ng/mL, 2.0 ng/mL, 1.0 ng/mL, 0.5 ng/mL and 0.25 ng/mL.
Enzyme-Labeled Streptavidin Solution The above-noted enzyme-labeled streptavidin diluent and the above-noted enzyme-labeled streptavidin stock solution were mixed in a ratio of 12 mL to 60 μL.
Substrate Solution The above-noted substrate solution B and the above-noted substrate solution A were mixed in a ratio of 6 mL to 6 mL.
Analyte Solution Using the above-described analyte diluent, the supernatants of cultures to which control and ligand candidate were added respectively were diluted by 25 times, and the supernatant of a culture to which pioglitazone was added as positive control was diluted by 50 times.

Only the strips of the antibody plates necessary for the analysis were taken out. After about 200 μL of the above-described washing solution was poured to each well of the antibody plate, the liquid in the well was absorbed and removed completely using a plate washer. This washing and absorption were performed once more. 100 μL of the standard solutions with respective concentrations and 100 μL of the diluted analytes were added to individual wells and measured in duplicate. Incidentally, the standard solutions always were measured for each measurement and each plate. After the antibody plate was covered with a plate seal and allowed to stand still for a reaction for 60 minutes at room temperature, the plate seal was removed from the antibody plate, followed by absorbing and removing completely the liquid in the well using the plate washer. Subsequently, about 200 μL of the washing solution was added to each well and immediately was absorbed and removed. This washing and absorption were repeated four more times. After 100 μL of the biotin labeled antibody solution was added to each well of the antibody plate, the antibody plate was covered with a plate seal and allowed to stand still for reaction for 60 minutes at room temperature. Similarly to the above, the washing of the wells and absorption were repeated five times. After 100 μL of the enzyme-labeled streptavidin solution was added to each well of the antibody plate, the antibody plate was covered with a plate seal and allowed to stand still for reaction for 60 minutes at room temperature. Similarly to the above, the washing of the wells and absorption were repeated five times. After 100 μL of the substrate solution was added to each well of the antibody plate and allowed to stand still for reaction for 15 minutes at room temperature, 100 μL of the reaction stop solution was added to each well of the antibody plate, and then the absorbance at 450 nm in each well was measured with a plate reader.

Using the results of quantitative determination with the Light Cycler™, the ratio of the respective mRNA expression amounts of aP2 and adiponectin with respect to the mRNA expression amount of 36B4 was calculated for each sample.

Figure 3:
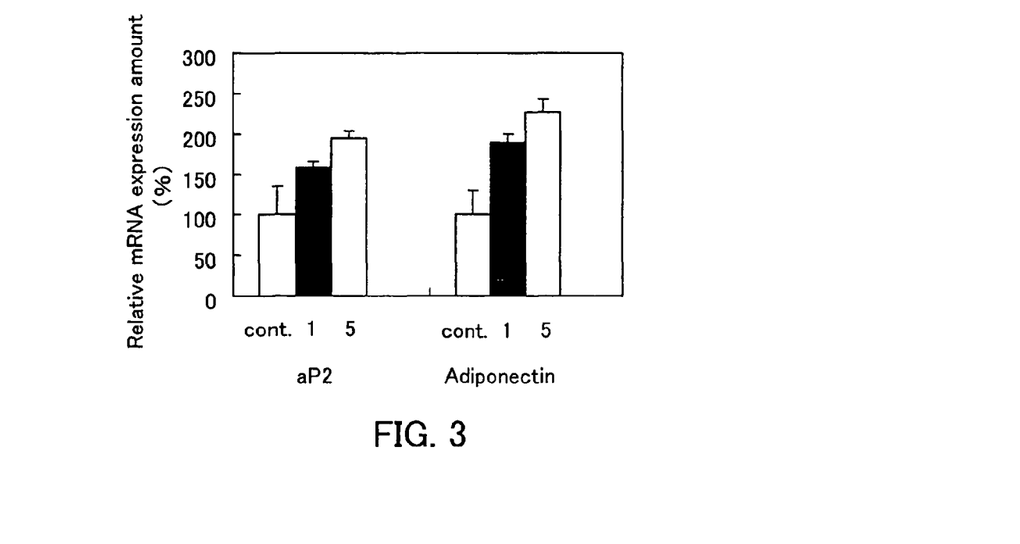
FIG. 3 is a graph showing adiponectin mRNA expression amounts by bergamottin in yet another example of the present invention.

The results of the calculation are shown in Table 3 below and the graph in FIG. 3. Also, the measurement results of the adiponectin secretion amount using ELISA are shown in Table 4 below and the graph in FIG. 4.

TABLE 3

| | Addition concentration | aP2 | Adiponectin |
|---|---|---|---|
| Non-treatment control | | 100 ± 34.3 | 100 ± 28.8 |
| Bergamottin | 1 μM | 157.5 ± 7.3 | 189.5 ± 9.7 |
| | 5 μM | 194.6 ± 9.0 | 227.2 ± 16.0 |
| | | | (average ± standard error) |

TABLE 4

Figure 4:
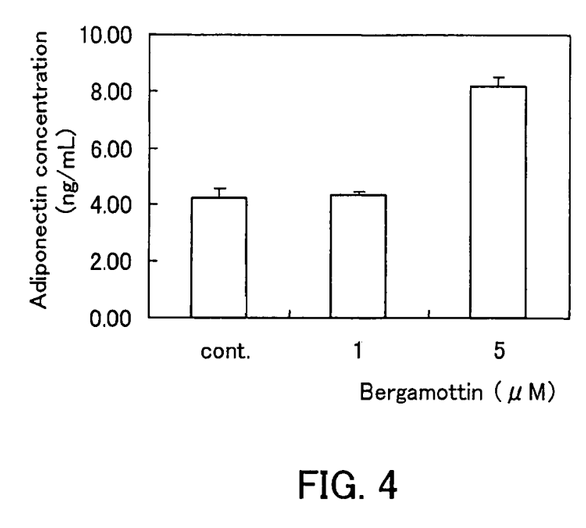
FIG. 4 is a graph showing an adiponectin secretion promoting effect of bergamottin in the above-noted example of the present invention.

| | Addition concentration | Secretion amount |
|---|---|---|
| Non-treatment control | | 4.27 ± 0.32 |
| Bergamottin | 1 μM | 4.37 ± 0.12 |
| | 5 μM | 8.14 ± 0.36 |
| | | (average ± standard error) |

From the results of measurement, when adipocytes cultured in the differentiation induction media to which 1 μM and 5 μM of bergamottin were added and adipocytes cultured in the non-treated control medium were compared, the addition of bergamottin was found to enhance the secretion of adiponectin in the adipocytes.

EXAMPLE 4

As described in the following, the present example confirmed the inhibition of VLDL secretion by bergamottin.

(Cell Culture)

FCS, a non-essential amino acid, sodium pyruvate and a glutamine solution were mixed such that the final concentrations of the FCS, the nonessential amino acid, the sodium pyruvate and the glutamine solution respectively were 10%, 1%, 1 mM and 2 mM, and added to an MEM medium (manufactured by SIGMA). They were mixed aseptically on a clean bench. In a 100 mm/Collagen-Coated Dish (trade name, manufactured by Iwaki Glass Works, Co.), the medium of HepG2 cells (human hepatic cells) that had been cultured to 80% to 90% confluence was removed with a pipette and washed with 2 mL of 1×PBS. After adding 2 mL of trypsin-EDTA and rotating the above-noted dish slowly so that trypsin-EDTA spread over the entire cells, this trypsin-EDTA was removed with a pipette. The dish was allowed to stand still for 15 minutes in a $CO_2$ incubator (37° C., 5%), and then 4 mL of a growth medium was added to this dish, followed by mixing by pipetting. Then, 2 mL of this mixture was added to each of two dishes to which 3 mL of a growth medium was added in advance. These dishes were covered with lids and moved crisscross so as to mix the content. The cells were checked using a microscope (manufactured by Olympus Corporation) and cultured in a $CO_2$ incubator (37° C., 5%). Three or four days later, after checking that 80% to 90% confluence was achieved using the microscope, subculture was carried out in a similar manner, followed by cell culture.

1. Time Course Experiment

HepG2 was cultured to reach 80% to 90% confluence, and the medium was removed with a pipette, followed by washing with 2 mL of 1×PBS and addition of 5 mL of a growth medium. Every 10 hours, 200 μL of the medium was collected and put into a tube (with a capacity of 1.5 mL). Using this sample, apoB100 was subjected to Western blotting and ELISA measurement.

(Western Blotting)

(1) SDS-PAGE

20 μL of the medium and a buffer containing 62.5 mM Tris-HCl (pH 6.8), 2% SDS, 10% glycerol, 5% (w/v)$_2$-mercaptoethanol and a 0.0005% BPB solution were put in a 1.5 mL tube so as to achieve the total amount of 30 μL, and stirred well. They were boiled in a hot water bath at 100° C. for 5 minutes. An acrylamide gel containing 7.5% SDS was set in Mini PROTEAN3 Cell (trade name, manufactured by Bio-Rad Laboratories, Inc.), and 300 μL of an electrophoresis buffer was poured so that the gel was soaked sufficiently. The electrophoresis buffer was prepared by diluting 30 mL of 10×Tris/Glycine/SDS buffer (manufactured by Bio-Rad Laboratories, Inc.) with 270 mL of $dH_2O$. Then, 30 μL of the sample and 5 mL of Rainbow Marker (trade name, manufactured by Promega Corporation) were dispensed quietly into the gel so as to perform electrophoresis. The condition of electrophoresis was a constant voltage of 200 V and a period of 40 to 45 minutes. Model 3000xi Computer Controlled Electrophoresis Power Supply (trade name, manufactured by Bio-Rad Laboratories, Inc.) was used as the power supply.

(2) Blotting

The gel that had been subjected to SDS-PAGE was soaked in a transcription buffer (2.42 mg/mL Tris base, 11.55 mg/mL Glycine, 20% methanol) for 15 minutes together with a PVDF membrane (Hybond TM-P PVDF transfer membrane; manufactured by Amersham Biosciences K.K.) until equilibrium was reached. Using a semidry flat transfer apparatus (manufactured by NIHON EIDO Co., Ltd.), the transcription was performed onto the PVDF membrane by a semidry method (40 mA/membrane, 90 minutes). This membrane was blocked with 5% skim milk (at room temperature for 1 hour). After the blocking, 5 mL of Ms×Hu Apolipoprotein B (manufactured by CHEMICON International, Inc.) that had been diluted with 5% skim milk by 1000 times was dispensed to the above-noted membrane and allowed to react at room temperature for 1 hour. The resultant membrane was washed with PBST three times (10 minutes, 20 minutes, 30 minutes), and 5 mL of anti mouse IgG-HRP (manufactured by Promega Corporation) that had been diluted with 5% skim milk by 5000-times was poured uniformly to the above-noted membrane and allowed to react at room temperature for 1 hour. The membrane was washed with PBST three times (10 minutes, 50 minutes, 10 minutes), and the detection was carried out by a chemiluminescence method using ECL+plus western blotting detection system (trade name, manufactured by Amersham Biosciences K.K.).

(ELISA)

First, a VLDL standard solution was prepared. The VLDL standard solution was prepared by diluting 1.169 mg/mL of human VLDL standard (trade name, manufactured by CHEMICON International, Inc.) with a growth medium. The dilution factors were 100, 1000, 10000, 100000 and 1000000.

A sandwich ELISA that recognized human apoB100 in the VLDL as an antigen was used. First, 100 μL of Moab×LDL Apolipoprotein B (ApoB) (manufactured under MONOSAN®) was dispensed in each well of ELISA PLATE, and the plate was sealed with a sterile seal and then allowed to stand still at 4° C. overnight. In the following, all the dispensing mentioned is for a single well. On the next day, 200 μL of Zepto Block (trade name, manufactured by ZeptoMetrix Corporation) was dispensed, and then the above-noted plate was sealed and allowed to stand still for 2 hours at room temperature for blocking. Subsequently, 100 µL of the medium and the VLDL standard solution were dispensed, and then the plate was sealed and allowed to stand still for 1 hour at room temperature. Washing with 200 µL of PBST and absorption using an aspirator were carried out five times in total. Then, 100 µL of Affinity Purified Anti-Apolipoprotein B (manufactured by Rockland Immunochemicals, Inc.) that had been diluted with PBS by 1000 times was dispensed and allowed to stand still for 1 hour at room temperature. After washing similarly to the above, 100 µL of Donkey Anti-goat IgG HRP (manufactured by Promega Corporation) that had been diluted with PBS by 5000 times was dispensed and allowed to stand still for 1 hour at room temperature. After washing similarly to the above, solutions A and B of TMB Microwell Peroxidase substrate (trade name, manufactured by Funakoshi Co., Ltd.) were mixed and allowed to stand still for 5 minutes at room temperature, and then 100 µL of this mixture solution was dispensed and allowed to stand still for 5 minutes at room temperature. 100 µL of 1M phosphoric acid solution was added to the above-noted mixture solution, and the absorbance at 450 nm was measured using wallac ARVOsx (trade name, PerkinElmer Life Sciences, PerkinElmer, Inc.). The mode of measurement was Photometry (450 nm, 1.0 S).

From the result of the Western blotting of human apoB100, a clear band was shown 20 hours or more after the start of culture. Also, from the result of the ELISA, a linear increase in the VLDL secretion amount was shown from the initiation of culture to about 50 hours thereafter. In view of these results, a collection time of the medium in a VLDL secretion inhibition experiment, which will be described below, was set to 30 hours.

2. VLDL Secretion Inhibition Experiment (Preparation of Medium Containing Bergamottin)

Into 15 mL centrifugation tubes, 3 mL of a medium was added, and further, bergamottin was added so as to achieve final concentrations of 10 µM, 20 µM and 50 µM. They were tumble-mixed to a sufficient degree, thus preparing media containing bergamottin. Also, as a control, a medium was prepared by adding the same amount of DMSO instead of bergamottin.

HepG2 was cultured to 80% to 90% confluence in a 100 mm/Collagen-Coated Dish (trade name, manufactured by Iwaki Glass Works, Co.). The medium was removed from the above-noted dish with a pipette and then HepG2 was washed with 2 mL of 1×PBS. Then, 2 mL of trypsin-EDTA was added, the above-noted dish was rotated slowly so that the trypsin-EDTA spread over the entire cells, this trypsin-EDTA was removed with a pipette, and the dish was allowed to stand still for 15 minutes in a $CO_2$ incubator (37° C., 5%). To this dish, 12 mL of a growth medium was added, followed by mixing by pipetting, and 1 mL of this mixture solution was dispensed in each well of Collagen-Coated Microplates 12Well/Flat Bottom (trade name, manufactured by Iwaki Glass Works, Co.). After the cells were checked using a microscope, the wells were cultured in a $CO_2$ incubator (37° C., 5%) for one to two days. After checking that 80% to 90% confluence was achieved using the microscope, a medium replacement was carried out by removing the medium and adding 800 µL of a medium containing bergamottin. Thirty hours later, 800 µL of the medium was collected from each well. Using this collected medium, the number of living cells were counted, and the Western blotting and the ELISA measurement were carried out similarly to the above. From the result of the ELISA, the ratio of the VLDL secretion amount between the measurement group and the non-treated control group (measurement group/control group) was calculated for each sample.

(Counting of the Number of Living Cells)

The measurement was made using CellTiter 96 Aqueous One Solution Cell Proliferation Assay (trade name, manufactured by Promega Corporation). First, 1.6 mL of CellTiter 96 Aqueous One Solution Reagent and 6.4 mL of a growth medium were added to a centrifugation tube (with a capacity of 15 mL) and stirred well. Then, 600 µL of the mixture solution was added to each well immediately after the medium was stirred, and incubated for 40 minutes in a $CO_2$ incubator (37° C., 5%). 100 µL of this mixture solution was dispensed to each of three wells of ELISA PLATE 96well (trade name, manufactured by Iwaki Glass Works, Co.), and the absorbance at 490 nm was measured. The measurement was made using wallac ARVOsx (trade name, PerkinElmer Life Sciences, PerkinElmer, Inc.), and the mode of measurement was Absorbance (490 nm, 1.0 S). The ratio of the number of living cells between the measurement group and the non-treated control group (measurement group/control group) was calculated for each sample.

Figure 5:
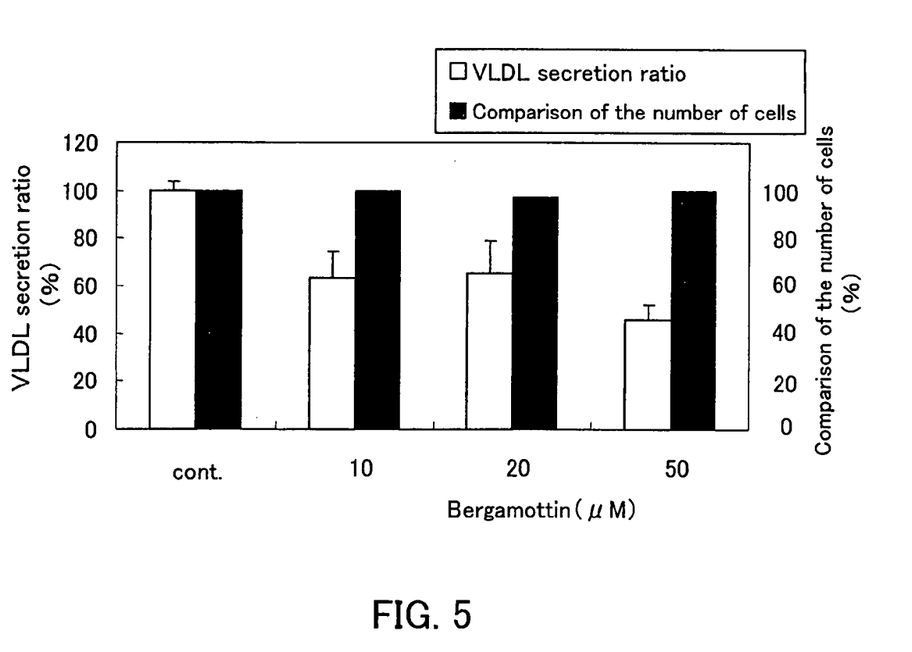
FIG. 5 is a graph showing a VLDL secretion inhibiting effect by bergamottin in yet another example of the present invention.

The results are shown in Table 5 below and the graph in FIG. 5.

TABLE 5

|  | Addition concentration | VLDL secretion ratio (%) | Number of living cells (%) |
|---|---|---|---|
| Non-treatment control | DMSO | 100 | 100 |
| Bergamottin | 10 µM | 63.4 ± 10.94 | 99.6 |
|  | 20 µM | 65.5 ± 13.21 | 97.2 |
|  | 50 µM | 45.9 ± 6.29 (average ± standard error) | 99.8 |

As becomes clear from the results above, the VLDL secretion was inhibited by bergamottin, and the degree of inhibition increased further as the bergamottin concentration rose.

Industrial Applicability

As described above, since the metabolic syndrome relieving agent according to the present invention has an excellent PPARα and PPARγ activity and a function of promoting adiponectin secretion, it is extremely effective in relieving a metabolic syndrome and can be used as a drug, a supplement, a functional food and a food additive for preventing and treating diseases such as insulin resistance, hyperinsulinism, type 2 diabetes, hypertension, hyperlipemia, arteriosclerosis, obesity and visceral fat obesity, for example. It should be noted that these effects are shown for not only humans but also other animals.

The invention claimed is:

1. A functional food for relieving a metabolic syndrome, the functional food comprising bergamottin,
   wherein the bergamottin is obtained by isolation and purification from at least one material selected from the group consisting of a fruit of a grapefruit, fruit juice thereof, and peel thereof,
   wherein the functional food contains an effective amount of the bergamottin to relieve the metabolic syndrome, and
   wherein the metabolic syndrome comprises at least one disease selected from the group consisting of arteriosclerosis and hypertension.

2. A food additive for relieving a metabolic syndrome, the food additive comprising bergamottin, wherein the bergamottin is obtained by isolation and purification from at least one material selected from the group consisting of a fruit of a grapefruit, fruit juice thereof, and peel thereof, wherein the food additive contains an effective amount of the bergamottin to relieve the metabolic syndrome, and wherein the metabolic syndrome comprises at least one disease selected from the group consisting of arteriosclerosis and hypertension.

3. The functional food according to claim 1, which activates a peroxisome proliferator-activated receptor (PPAR).

4. The functional food according to claim 3, wherein the PPAR comprises at least one of a PPARα and a PPARγ.

5. The food additive according to claim 2, which activates a peroxisome proliferator-activated receptor (PPAR).

6. The food additive according to claim 5, wherein the PPAR comprises at least one of a PPARα and a PPARγ.

7. A functional food for a human useful for relieving a metabolic syndrome, the functional food comprising bergamottin, wherein the functional food contains an effective amount of the bergamottin to relieve the metabolic syndrome of the human, wherein the bergamottin is obtained by isolation and purification from at least one material selected from the group consisting of a fruit of citrus fruit, fruit juice thereof, and peel thereof, wherein the citrus fruit is at least one selected from the group consisting of a grapefruit and a bergamot, and wherein the metabolic syndrome comprises at least one disease selected from the group consisting of arteriosclerosis and hypertension.

8. The functional food according to claim 7, which activates a peroxisome proliferator-activated receptor (PPAR).

9. The functional food according to claim 8, wherein the PPAR comprises at least one of a PPARα and a PPARγ.

10. A food additive for a human useful for relieving a metabolic syndrome, the food additive comprising bergamottin, wherein the food additive contains an effective amount of the bergamottin to relieve the metabolic syndrome of the human, wherein the bergamottin is obtained by isolation and purification from at least one selected from the group consisting of a grapefruit and a bergamot, and wherein the metabolic syndrome comprises at least one disease selected from the group consisting of arteriosclerosis and hypertension.

11. The food additive according to claim 10, which activates a peroxisome proliferator-activated receptor (PPAR).

12. The food additive according to claim 11, wherein the PPAR comprises at least one of a PPARα and a PPARγ.

* * * * *